United States Patent [19]

Tucker

[11] Patent Number: 4,924,107
[45] Date of Patent: May 8, 1990

[54] SYSTEM FOR INSPECTING THE INSIDE SURFACES OF A CONTAINER FOR DEFECTS AND METHOD THEREFOR

[75] Inventor: John W. Tucker, Louisville, Colo.

[73] Assignee: Ball Corporation, Muncie, Ind.

[21] Appl. No.: 254,952

[22] Filed: Oct. 7, 1988

[51] Int. Cl.⁵ .................................................. G01N 21/88
[52] U.S. Cl. ..................................... 250/572; 356/241
[58] Field of Search ................... 250/223 B, 562, 563, 250/571, 572; 356/240, 241; 209/576

[56] References Cited

U.S. PATENT DOCUMENTS 3,923,158 12/1975 Fornåå .............................. 250/223 B
4,786,801 11/1988 Shay ................................. 250/223 B
4,811,251 3/1989 Minato ................................ 356/240

OTHER PUBLICATIONS

Fast Track—High-Speed Automated Inspection System by Ball Industrial Systems Division—Printed in USA 7/88.

Primary Examiner—David C. Nelms
Attorney, Agent, or Firm—Dorr, Carson, Sloan & Peterson

[57] ABSTRACT

A system for inspecting a plurality of horizontal regions on the inside surfaces of an object such as an aluminum beverage can for defects. This system utilizes a plurality of cameras with each camera focused, in a field of view, on one of the plurality of horizontal regions in the object, the light for illuminating the inside of the object, an including dot for selectively masking out areas of reflected interfering light, and a processor for analyzing the captured image of the horizontal region when illuminated.

19 Claims, 7 Drawing Sheets

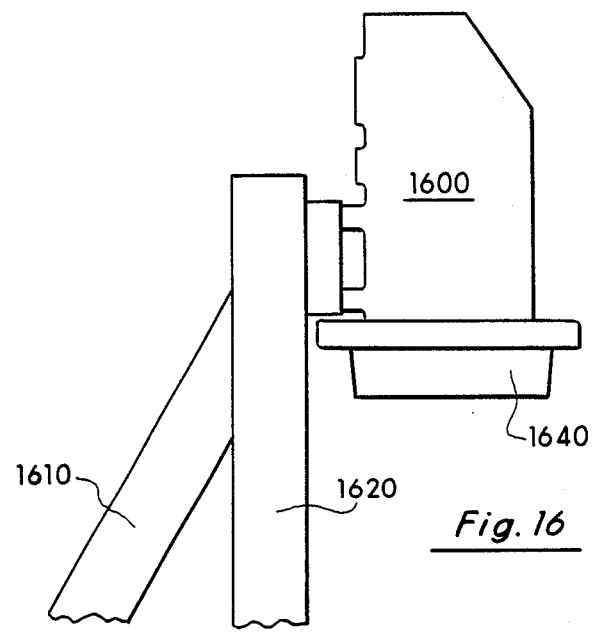
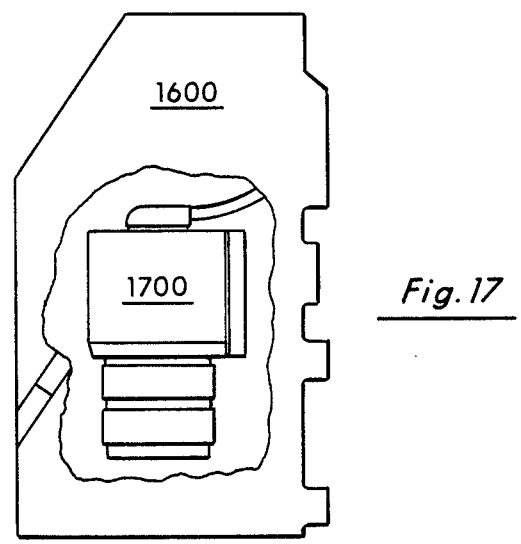

SYSTEM FOR INSPECTING THE INSIDE SURFACES OF A CONTAINER FOR DEFECTS AND METHOD THEREFOR

BACKGROUND OF THE INVENTION

1. Field of the Invention

The present invention relates to a system for the inspection of the inside surfaces of objects for defects and, more particularly, for the inside surface inspection of containers such as aluminum beverage cans for a variety of surface imperfections and defects.

2. Statement of the Problem

A need exists in manufacturing environments for high speed inspection of the inside surfaces of objects such as aluminum beverage cans. Conventional manufacturing processes move such aluminum beverage cans along a conveyor at line speeds of 1200 to over 2000 cans per minute. During the manufacturing process for the aluminum beverage cans, a number of inside surface conditions can be created which would cause the can to be rejected. The inside surfaces of the cans, for example, should be round and free of physical defects such as dents and the like and the inside surfaces should be free of grease, oil, blistering, or debris. In addition, the flange should be free of knockdowns.

Complicating the problem of inside surface inspection is the geometry of the beverage can. A typical beverage can such as that shown in FIG. 1, has a number of curved surfaces which make surface inspection difficult especially when illuminated light is delivered into the can and the reflection off such curved surfaces makes it difficult to inspect nearby or adjoining surfaces.

Hence, a need exists for a high speed inside surface inspection system which does not interfere with the operation of a normal conveyor line carrying beverage cans and which is capable of inspecting the surfaces for small sized defects such as, for example, 0.040 inches in a fashion that does not interfere or obstruct the manufacturing process of the cans.

3. Solution to the Problem

The present invention provides a solution to the above problem, in one embodiment, by providing a series of three physically spaced cameras along a conventional conveyor line. Depending upon the inside surface of the object being inspected, two or more cameras can be utilized. In addition, one camera could be utilized to inspect a selected area inside the object such as the moat of an aluminum beverage can. Each camera captures an image of the inside of the beverage can at a different horizontal location in the can. Undesirable and interfering reflections of light from the illumination of the interior of the can are selectively masked out so that the captured image of the area next to the severe reflection can be thoroughly analyzed.

The system of the present invention is capable of inspecting for defects and imperfections down to about 0.040 inches in size, but the invention is not limited to this resolution. The system of the present invention does not interfere with the travel of the cans along the conveyor line unless a defect is sensed in a given can which is then rejected from the line.

SUMMARY OF THE INVENTION

A system for inspecting the inside surfaces of a container for defects is set forth for use on a conveyor line moving a plurality of containers. Each of the containers corresponds to a standard aluminum beverage can having an open top, a flange, a neck, a sidewall, a chime, a moat, and a dome bottom. In some aluminum beverage cans the necking structure is not utilized.

The system utilizes a first camera, processor, and monitor combination located at a first position on the conveyor line for determining through the open top of the can whether any defects are present in a first horizontal region inside the container. In the disclosed approach, the first horizontal region is the moat and chime area around the dome bottom of the can. The camera captures an image of the moat and chime and the processor analyzes the image for the presence of any defects.

A second camera, processor, and monitor combination is located at a second position on the conveyor line for determining through the open top of the can, when the can moves under the second camera, whether any defects are present in a second horizontal region inside the can. The second horizontal region comprises the lower portion of the sidewall of the can and the dome bottom. The second camera captures the image of the lower portion of the sidewall and of the dome and the second processor analyzes the captured image for the presence of any defects.

A third camera, processor, and monitor combination is located at a third location on the conveyor line for determining through the open top of the can, when the can is positioned under the camera, the presence of any defects in a third horizontal region inside the can. The third horizontal region includes the upper portion of the sidewall, the neck, and the flange of the can. The third camera captures an image and the third processor analyzes that image for the presence of any defect.

In the event the first, second and third processors detect the presence of any defects, the system will cause the can containing the defect to be ejected from the conveyor line. The above system can be modified to inspect the inside surfaces of any object moving along a conveyor line. In the case of cameras 1 and 3, an occluding dot is placed in the field of view of the focused camera in the region to mask out light from the reflected dome which would otherwise mask the moat and chime area inspection around the dome or interfere with the inspection of the flange and neck area of the can.

Under the method of the present invention, a method for inspecting a selected area on the inside surface of an object such as the aluminum beverage can, through an opening in the object is set forth. The method comprises the steps of illuminating the inside of the object through the opening with light, locating the opening of the object under a camera wherein the lens of the camera is focused in the field of view for the selected area of inspection, if necessary, placing an occluding dot in the field of view of the focused camera to mask out light reflected from the interfering reflected surfaces, capturing an image of the illuminated selected area with a camera, and analyzing the captured image of the selected area with a processor for the presence of any defects.

DESCRIPTION OF THE DRAWING

FIG. 16 sets forth the camera housing of the present invention; and

FIG. 17 sets forth the inside configuration of the camera housing of FIG. 16.

DETAILED SPECIFICATION

1. General Discussion

Figure 1:
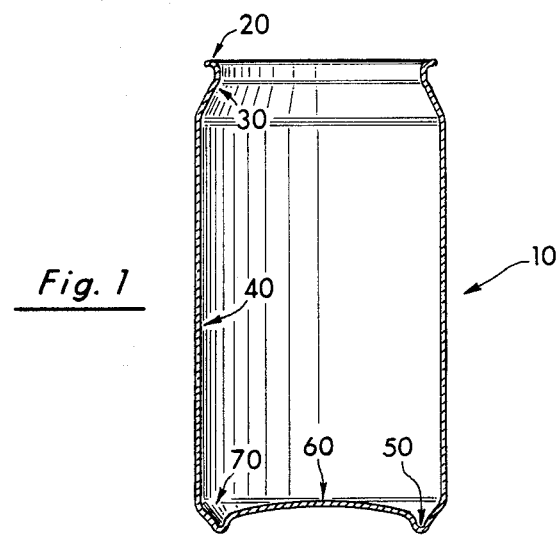
FIG. 1 sets forth, in cross-section, a side view of a conventional aluminum beverage can.
Figure 2:
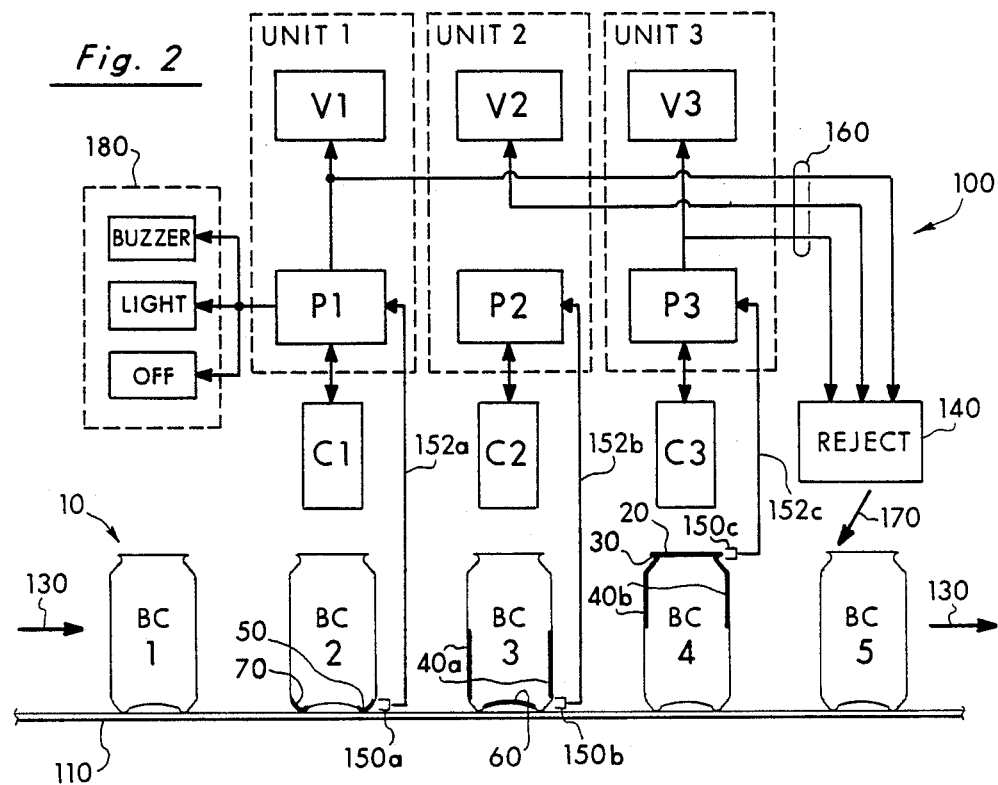
FIG. 2 sets forth, in block diagram format, the system of the present invention inspecting a plurality of cans moving along a conveyor belt.

FIG. 1 sets forth a conventional beverage can 10 which has five major areas that require inspection. These areas of inspection include the flange 20, the neck 30, the sidewall 40, the moat or nestled area 50, the chime 70 and the dome 60. For a can to pass inside inspection for defects, the flange 20 must be round and free of knock-downs. The neck area 30 must be free of necker grease. The sidewall 40 must also be free of dents, grease, oil, or printing on the inside. The chime 70, moat or nestled area 50 and dome bottom 60 as well as the above areas must be free of imperfections such as caused from the inner coating blistering and also free of any debris. The inside beverage can inspection system 100 of the present invention is shown in FIG. 2 in conjunction with a conventional conveyor belt 110 carrying a plurality of cans 10 in the direction of arrow 130. The inside beverage can inspection system 100 of the present invention includes a plurality of three cameras C1, C2, and C3; a plurality of three processing systems P1, P2, and P3; and a reject mechanism 140. In addition, video monitors V1, V2, and V3 are utilized.

In a typical manufacturing line situation, the conveyor belt 110 moves the cans 10 which are randomly spaced along at conventional line speeds up to over 2000 cans per minute. The system 100 of the present invention operates at these speeds and if conveyor belts could be designed to go faster, the present invention is capable of operating at 3200 cans per minute. The conveyor 110 is typically a vacuum conveyor with side guides to position, side-to-side, the cans under the cameras.

Each unit of processors and video monitors, (such as Unit 1 for P1-V1) are conventionally available from Ball Corporation, Industrial Systems Division, 9343 West 108th Circle, Westminster, Colo. 80020 as a product trademarked as FAST TRACK. Hence, in the system 100 of the present invention three FAST TRACK units (Units 1, 2, and 3) are utilized. In operation and as illustrated in FIG. 2 for a given time frame, Unit 1 with camera C1 visually inspects the moat 50 and chime 70 as shown by the darkened area inside can BC2. Unit 2 with camera C2 inspects the lower sidewall 40a and the dome 60 on the inside of can BC3. Unit 3 with camera C3 inspects the upper sidewall 40b, the neck 30, and the flange 20 on the inside of can BC4.

As can BC2 moves along the conveyor belt 110 in the direction of arrow 130, the bottom of the can is sensed by a photo detector 150a which delivers a signal over line 152a to processor P1. Processor P1 then activates camera C1 to capture an image of the moat 50 and chime 70. As can BC2 travels along conveyor belt 110, the bottom of the can will then activate photocell 150b delivering a signal over 152b to processor P2 which causes camera C2 to capture an image of the lower sidewall 40a and the bottom dome 60. Finally, as can BC2 travels along conveyor 110, the neck 30 of the can activates photocell 150c causing a signal to be delivered over line 152c into processor P3. Processor P3 then causes camera C3 to capture an image of the upper sidewall 40b, the neck 30, and the flange 20.

Should can BC2 have an unacceptable defect or flaw as determined by processor P1, P2, or P3; an appropriate reject signal is delivered over bus 160 to the reject circuit 140 which causes can BC2 to be pushed out from the conveyor belt 110 in the direction of arrow 170. A number of conventional reject mechanisms 140 could be utilized under the teachings of the present invention. In the event that can BC2 passes the three separate inside surface inspections, it continues along on conveyor belt 110 in the direction of arrow 130.

It is to be expressly understood that while FIG. 2 illustrates one arrangement of the cameras inspecting the interior surfaces of the can 10, that other spatial arrangements such as C2-C1-C3 or C3-C2-C1 could likewise be utilized.

Figure 3:
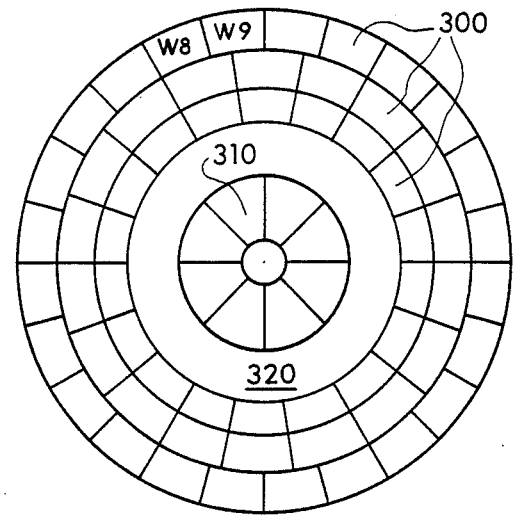
FIG. 3 is a photograph of crescent-shaped windows for analyzing the lower sidewalls and dome of an aluminum beverage can.

The conventionally available FAST TRACK units convert the image from the video cameras into binary images by applying an edge detection algorithm. The resulting analyzed images are displayed in the monitors V1, V2, and V3. Typically, each monitor is a black and white monitor and the operator of the system can define inspection windows on this monitor. For example, in FIG. 3, the operator defined a plurality of crescent-shaped windows 300 and 310 to conform to the shape of the surface area inside of the can being inspected. FIG. 3 sets forth the crescent-shaped windows 300 for inspecting the area of the lower sidewalls 40a and the windows 310 for inspecting the dome 60. The processor P2 uses these windows to evaluate the captured image from camera C2. The area 320 is not analyzed as this corresponds to the moat 50 and chime 70.

The creation of the windows 300 and 310 are conventional with the FAST TRACK unit and the operator can define up to 127 independent windows of any shape and set a predetermined tolerance for part rejection for each window. During inspection, the captured images are delivered to the processor and an analysis of each window in the image is performed.

Rejection of a can occurs when the operator sets a predetermined tolerance in each of the processors P1, P2, and P3. The processors will then count the defects or imperfections in the area of inspection that exceeds the preset tolerances, the processor will cause the can to be rejected. Statistical counters are updated after every can is ascertained to pass or be rejected. The processor, however, stores in memory the number of rejected cans and the window number that was rejected.

Each processor P1, P2, and P3 can be configured to turn on a light, a buzzer, or to shut off the conveyor line 110 as shown by control 180 in FIG. 2 in dotted lines for processor P1. The selection of a buzzer, a light, or an off switch for the conveyor belt 110 is dependent upon the nature of the installation and is customer defined. In addition, statistical information from each processor can be sent to an external database via a conventional RS232 port, not shown, or stored by the processor internally in a non-volatile memory or floppy diskette.

2. Detailed Discussion of Operation

In the following, the predetermined areas of inspection by each of the cameras C1, C2, and C3 of the system 100 will be more fully discussed.

A. Camera 1 Predetermined Area of Inspection

Figure 4:
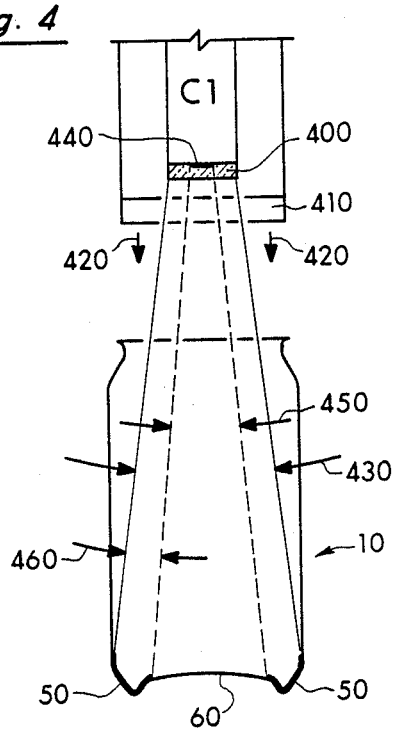
FIG. 4 is an illustration setting forth the inspection of an aluminum beverage can with a first camera in a first horizontal region of the can.

In FIG. 4, the details for the inspection of the moat or nestled area 50 of beverage can 10 is shown. The camera C1 has a lens 400 which provides a field of view for the moat 50 and the dome 60. Illuminating optics 410 such as a fiber optic ring in camera C1 produces light 420 which illuminates the inside of the can 10. The fiber optic ring is appropriately strobed by the processor and this arrangement is used in all three cameras for illumination. The field of view of camera C1 is defined by arrows 430 which includes both the moat 50 and chime 70 and the dome area 60. With camera C1 focused on the moat area 50, the light 420 reflects off the dome 60 thereby interfering with the inspection of defects in the moat 50. A mask or occulting dot 440 is utilized behind or in front of lens 400, or on the sensor of the camera to block out the image of the dome 60. The eliminated field of view is shown in FIG. 4 by arrows 450. Hence, a ring-shaped field view as shown by arrows 460 provide the video image to be captured by camera C1 and analyzed by processor P1. It can be observed that under the teachings of the present invention the field of view can be suitably adjusted through choice of lens and use of a suitable mask to selectively analyze a predetermined area of interior surface.

In the preferred embodiment, camera C1 is located approximately 7½ inches above the conveyor surface for inspecting a standard 12 oz. aluminum beverage can 10 and achieves a resolution nominally of 0.030 inches. The diameter of the dot 440 is 150 mils. The lens is 16 mm. Visual inspection of the moat 50 and chime 70 detects general trash contamination, blisters, or severe distortions. The systems can be adjusted for 16 oz. cans or other objects suitable for inside surface inspection.

Figure 5:
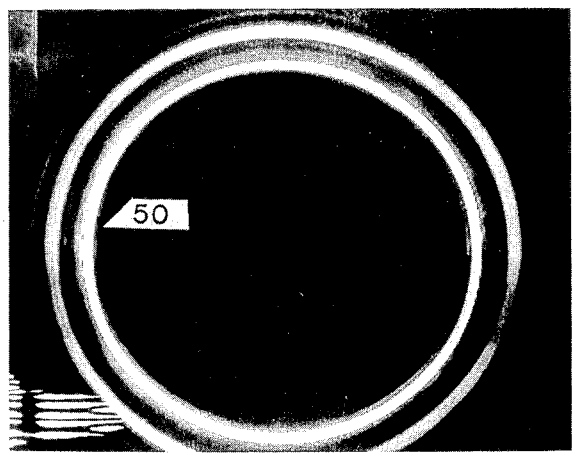
FIGS. 5, 6 and 7 are photographs showing the analysis for the moat and chime area of an aluminum beverage can.
Figure 6:
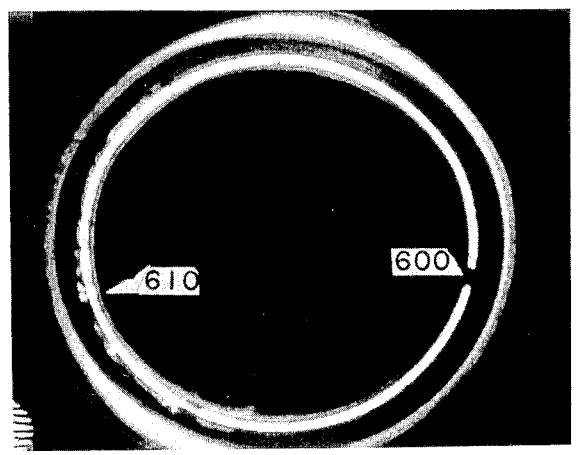
Figure 7:
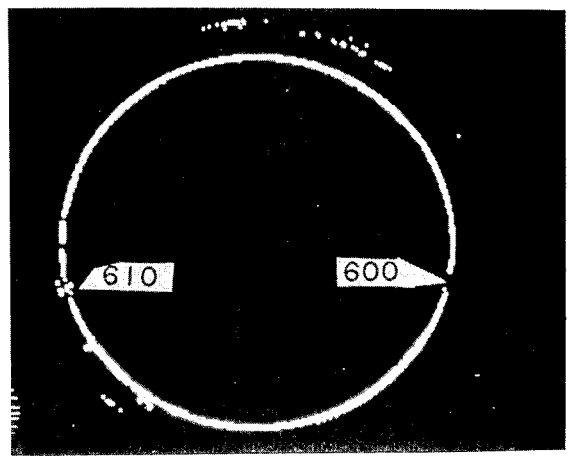

For example, in FIG. 5, a captured camera image of the moat area 50 of a good can is shown. In FIG. 6, cardboard dust 600 exists in the moat 50 as well as blisters 610. FIG. 7 is an analyzed image from processor P1 of the camera image of FIG. 6. In FIGS. 5 through 7, the eliminated field of view 450 is shown thereby leaving the moat area 50 for analysis.

It is to be expressly understood that the method discussed above for camera C1 detects through the open top of the can whether any defects are present in a first horizontal region. The first horizontal region in the can 10 comprises the moat 50 and the chime 70. In order to fully evaluate these regions the interfering reflected light from the dome caused by the illumination is masked out by the occluding dot. In the case of another object being illuminated such as a food container, camera C1 is designed to capture a first image of a predefined lower region in the container.

However, in the case of an aluminum beverage can 10, the method of the present invention includes the steps of illuminating the inside of the can with light from the optics ring 410, locating 150a the can under the camera C1, placing an occluding dot 440 in the field of view 460 of the camera which is focussed on the moat and chime, capturing an image of the illuminated moat and chime, and then analyzing the captured image for defects.

B. Camera 2 Predetermined Area of Inspection

Figure 8:
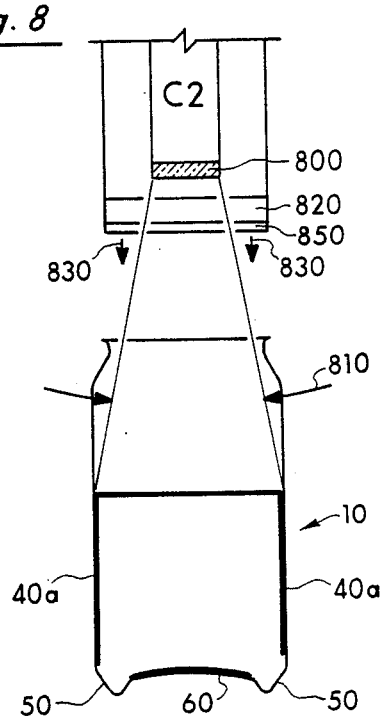
FIG. 8 is an illustration of a second camera inspecting an aluminum beverage can in a second horizontal region of the can.

In FIG. 8, details of camera C2 inspecting a can 10 in the lower sidewall 40a and bottom dome 60 are shown. Camera C2 obtains a resolution which is nominally 0.04 inches minimum distance except the bottom one inch of the sidewalls where resolution degrades to about 0.060 inches. The types of defects detected include grease spots, regions of no spray, partial spray, or over spray, general flaws, severe dents, internal lithography and internal base coat.

In FIG. 8, the lens 800 provides a field of view 810 which includes lower sidewalls 40a, moat 50, and the bottom dome 60. The optic ring 820 delivers light 830 into the inside of the can 10 thereby illuminating the sidewalls 40a and the bottom 60. In this field of view 810, the moat 50 and chime 70 cannot be inspected due to the light reflections off the dome 60 by the light 830. Hence, the analysis by Unit 2 is limited to the lower sidewalls 40a and the bottom dome 60. Again, the area to be inspected is captured by camera C2 and is delivered into processor P2. In addition, a circular polarized lens 850 is placed over light 820 to cut down on the intensity of the reflections from the dome.

In the preferred embodiment, camera C2 is located approximately 7½ inches above the surface of the conveyor. The lens 820 is 6.5 mm.

Figure 9:
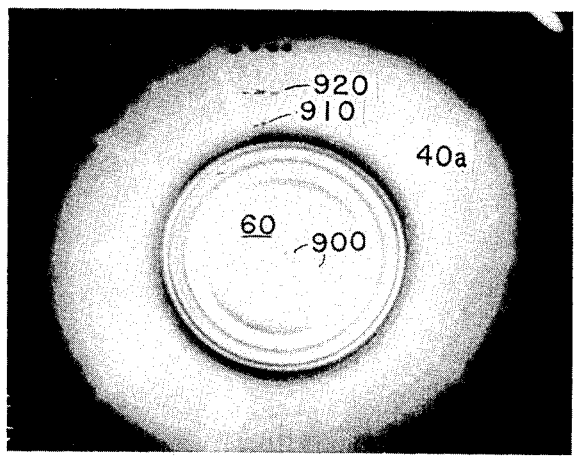
FIGS. 9, 10 and 11 are photographs showing the analysis of the lower sidewall and dome of an aluminum beverage can.
Figure 10:
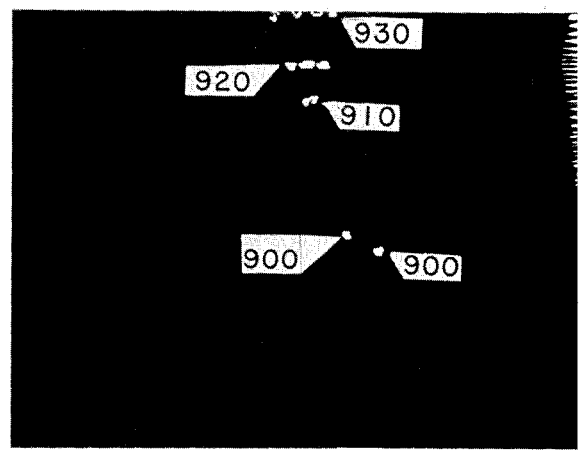
Figure 11:
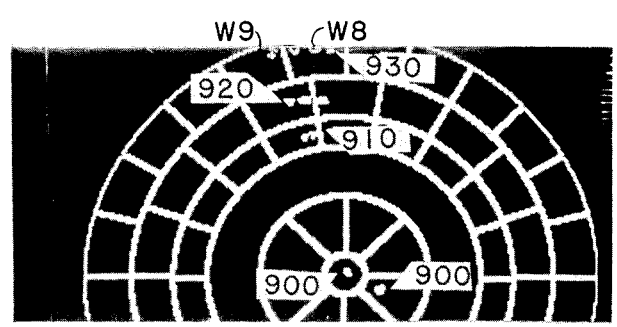

In FIG. 9, the camera image of the dome 60 and bottom sidewalls 40a are shown with 0.040 inch dots 900 placed on the inside of the can. Two dots were placed on the dome. One dot was placed on the bottom of the sidewall, two dots were placed one inch up the sidewall, three dots were placed two inches up the sidewall, etc. Notice the lack of any image in FIG. 9 corresponding to the moat area 50. In FIG. 10, the processor P2 has analyzed the image of FIG. 9 resulting in the detection of the dots. In FIG. 11, the windows of FIG. 3 are overlaid on the analyzed areas of FIG. 10 thereby showing the location of the defects. In FIG. 9, the captured image shows the one dot 900 which marks the bottom of the sidewall, two dots 910 which mark one inch up the sidewall, three dots 920 which marks two inches up the sidewall, and four dots 930 which are four inches up.

It is to be expressly understood that the method of using camera C2 detects through the open top of the can the existence of defects in a second horizontal region inside the object. In the case of can 10, this includes examination of the dome (60) for defects as well as the lower portion (40a) of the sidewall (40). Camera C2 is focussed in the second horizontal region and, in the preferred embodiment, a circular polarized filter is used to lower the intensity of the reflected light.

C. Camera 3 Predetermined Area of Inspection

Figure 12:
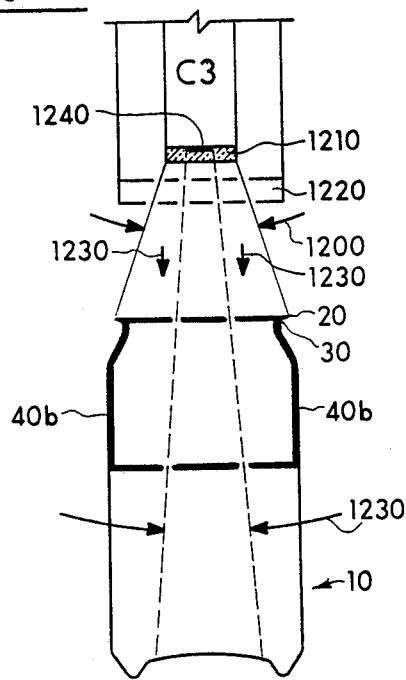
FIG. 12 is an illustration of a third camera inspecting a third region of an aluminum beverage can.

The details of camera 3 analyzing a can 10 are shown in FIG. 12. Camera 3 inspects the upper sidewall 40b, the neck 30, and the flange 20. Resolution is nominally obtained at 0.040 inches minimum dimension. The following types of defects are detected: knocked-down flange, dents, internal lithography, necker grease, out of round, no spray, partial spray, and base coat.

In FIG. 12, the camera C3 has a field of view shown by arrows 1200. The lens is preferably 4.8 mm. and the distance from the lens to the surface of the conveyor is 7⅜ inches. The optics 1220 again provide light 1230 which illuminates the inspected area. An occulting dot 1240 is placed behind the lens or in front of the lens, or on the sensor of the camera C3. The dot 1240 is 100 mils in diameter. Again, the dot eliminates the interfering reflection of the light by the dome 60. The field of view being eliminated is shown by arrows 1230.

Figure 13:
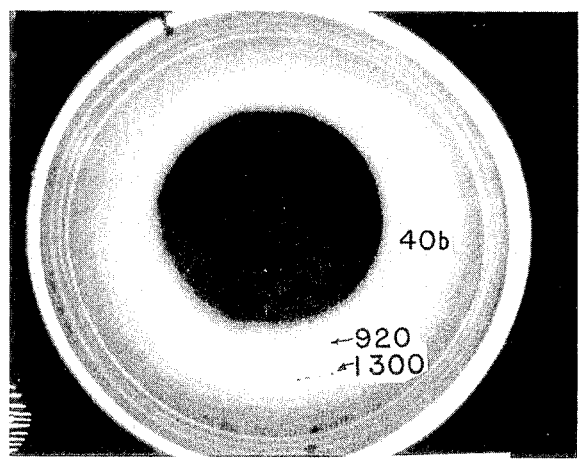
FIGS. 13 and 14 are photographs showing the analysis of the upper sidewall, neck and flange of an aluminum beverage can.
Figure 14:
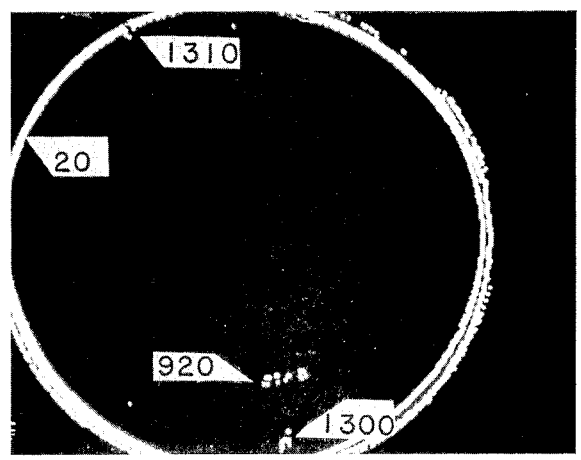

In FIG. 13, the captured camera image shows three dots 920 and four dots 930 on the sidewall. A 0.040 strip 1300 is detected on the neck as shown. Note, that the area 40b slightly overlaps with area 40a. The analyzed image by processor P3 is shown in FIG. 14.

Under the method of operation set forth for camera C3, the camera is focussed on a third horizontal region in the object for the analysis of defects which for the aluminum can 10 comprises the neck 30, the flange 20 and the upper portion 40b of the sidewall 40. Again, the interfering reflected light is masked out by a suitably placed occluding dot in the camera's field of view.

3. Example of Operating Results

In Appendix 1, is set forth a table which is an actual statistical printout by processor P2 of the analyzed picture of FIG. 11. The limits of the Lower and Upper columns shows where the inspection limits were set for each window by the operator. During the inspection process all bright pixels within a window are counted by the processor and placed in the "Actual" column. In the example of Appendix 1, the operator placed the Lower tolerance to 0 and the Upper tolerance to 5. Windows 8 and 9 in Appendix 1 are out of limits and these two windows are illustrated in FIG. 11. Windows 8 and 9 contain the four 0.040 dots 930 on the lower sidewall 40a.

At the bottom of the printout shown in Appendix 1, there is a continuous update of information (i.e., the number of inspected, accepted and rejected cans). This printout can also be viewed on a monitor V2. In the example of Appendix 1, 22,666 cans have been inspected, 4,481 cans have been accepted, and 18,185 cans have been rejected.

4. Alternate Embodiment

Figure 15:
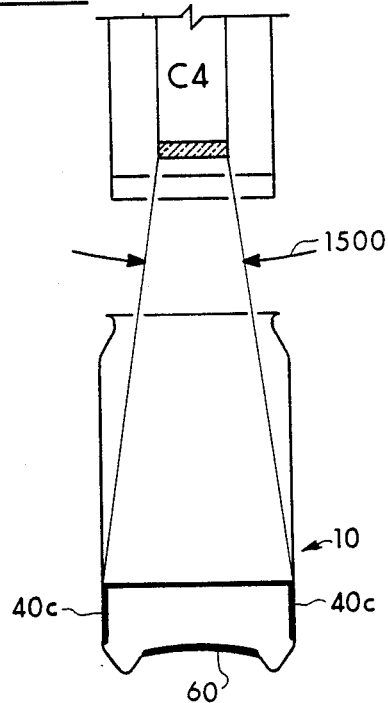
FIG. 15 is an illustration of a fourth camera inspecting a fourth horizontal region of an aluminum beverage can.

In FIG. 15, a fourth camera may be added in an alternate embodiment. As mentioned, camera C2 which inspects the lower sidewall 40a and the dome 60 has an upper resolution of 0.040 inches which degrades to 0.060 inches at the lower part of sidewall 40a. In FIG. 15, a fourth camera C4 is added to the system with a corresponding processor P4 and video monitor V4. Camera C4 has a field of view of 1500 which increases the resolution of the lower sidewall portion 40c to 0.040 inches. The light source and light is not shown in FIG. 15 but would be provided as priorly discussed.

5. Physical Construction of Camera

In FIGS. 16 and 17, the physical details for the mounting of any one of the three cameras is set forth.

In FIG. 16, the camera housing 1600 is mounted to a camera bracket 1610 which extends downwardly and rearwardly from a second camera bracket 1620. The camera housing 1600 is conventionally mounted at 1630 to the bracket 1620. Disposed around the bottom of the camera housing 1600 is the strobe ring 1640 which provides the illuminated light into the interior of the can.

The details of the FAST TRACK camera housing 1600 are shown in FIG. 17 which illustrates the position of the camera head 1700 having a camera lens 1710.

It can be readily observed that the present invention is capable of inspecting selected horizontal zones on the inside of a can or an object for the inspection of certain flaws, or form of material defects.

While preferred embodiments of the present invention have been shown, it is to be expressly understood that modifications and changes may be made thereto and that the present invention is set forth in the following claims.

APPENDIX 1

| Fast Track V | Window | Lower | Actual | Upper | Result | Level | Corporation |
|---|---|---|---|---|---|---|---|
| | | Display limits for defined windows (transition) | | | | | |
| 1 - Change | 2 | 0 | 0 | 5 | IN | 2 | |
| 2 - Edit g | 3 | 0 | 0 | 5 | IN | 2 | |
| 3 - Define | 4 | 0 | 0 | 5 | IN | 2 | |
| 4 - Displa | 5 | 0 | 0 | 5 | IN | 2 | |
| 5 - Set/di | 6 | 0 | 0 | 5 | IN | 2 | |
| 6 - Inspec | 7 | 0 | 0 | 5 | IN | 2 | |
| 7 - File m | 8 | 0 | 16 | 5 | HIGH | 2 | |
| 8 - Exit p | 9 | 0 | 8 | 5 | HIGH | 2 | |
| | 10 | 0 | 0 | 5 | IN | 2 | |
| | 11 | 0 | 0 | 5 | IN | 2 | |
| | 12 | 0 | 0 | 5 | IN | 2 | |
| | 13 | 0 | 0 | 5 | IN | 2 | |
| | 14 | 0 | 0 | 5 | IN | 2 | |
| | 15 | 0 | 0 | 5 | IN | 2 | |
| | 16 | 0 | 0 | 5 | IN | 2 | |
| | 17 | 0 | 0 | 5 | IN | 2 | |

Ins: 22666 Acc: 4481 (19.770%) Rej: 18185 (80.230%) Rate: 0    13:00:03
Cam:2 Ins:DDDD Int:1    Next:00:00:00 Rpt:D
\<PgDn\> next page, \<PgUp\> prev page,    \<Esc\> exit, \<F1\> help

I claim:

1. A system for inspecting a selected area on the inside surface of an object through an opening in the object, the object having a reflective surface which when illuminated interferes with the inspection of the selected area, said system comprising:
   means for illuminating the inside of the object through said opening with light,
   a camera, said camera having a lens,
   means for locating the opening of said object under the lens of said camera, said lens being focussed in the field of view for the selected area, means in said field of view of said focussed camera for masking out light reflected from said interfering reflective surface,
said camera capturing an image of the illuminated selected area, and
means for analyzing said captured image of said selected area for defects.

2. The system of claim 1 wherein a circular polarizer is placed after the illuminating means in said field of view.

3. A system for inspecting the inside surfaces of a container for defects, said container having an open top, a flange (20), a necking area (30), a sidewall (40), a moat (50), a chime (70) and a dome bottom (60), said system comprising:
first means (Unit1, C1) for determining through said open top whether said defects are present in a first horizontal region inside said container by analyzing reflected light from said first horizontal region through said open top, said first horizontal region comprising said moat and said chime,
second means (Unit 2, C2) for determining through said open top whether said defects are present in a second horizontal region inside said container by analyzing reflected light from said second horizontal region through said open top, said second horizontal region comprising the lower portion (40a) of said sidewall and said dome,
third means (Unit 3, C3) for determining through said open top whether said defects are present in a third horizontal region inside said container by analyzing reflected light from said third horizontal region through said open top, said third horizontal region comprising the upper portion (40b) of said sidewall, said necking area, and said flange,
means operative upon a determination by said first, second, or third determining means that a defect is present for rejecting said container.

4. The system of claim 3 wherein said second determining means includes a circular polarizer.

5. A system for inspecting the inside surfaces of a container for defects, said container moving on a conveyor line and said container having an open top, a sidewall (40), and a bottom (60), said system comprising:
first means (Unit1, C1) located at a first position on said conveyor line for determining through said open top whether said defects are present in a first horizontal region inside said container by analyzing reflected light from said first horizontal region through said open top, said first horizontal region including a portion of said bottom of said container,
second means (Unit 2, C2) located at a second position on said conveyor line for determining through said open top whether said defects are present in a second horizontal region inside said container by analyzing reflected light from said second horizontal region through said open top, said second horizontal region including a lower portion of said sidewall,
third means (Unit 3, C3) located at a third position on said conveyor line for determining through said open top whether said defects are present in a third horizontal region inside said container by analyzing reflected light from said third horizontal region through said open top, said third horizontal region including an upper portion of said sidewall,
means operative upon a determination by said first, second, or third determining means that a defect is present for rejecting said container from said conveyor line.

6. A system for inspecting the inside surfaces of a container for defects, said container moving on a conveyor line and said container having an open top, a flange (20), a necking area (30), a sidewall (40), a moat (50), a chime (70) and a dome bottom (60), said system comprising:
first means (Unit1, C1) located at a first position on said conveyor line for determining through said open top whether said defects are present in a first horizontal region inside said container by analyzing reflected light from said first horizontal region through said open top, said first horizontal region comprising said moat and said chime,
second means (Unit 2, C2) located at a second position on said conveyor line for determining through said open top whether said defects are present in a second horizontal region inside said container by analyzing reflected light from said second horizontal region through said open top, said second horizontal region comprising the lower portion (40a) of said sidewall and said dome,
third means (Unit 3, C3) located at a third position on said conveyor line, for determining through said open top whether said defects are present in a third horizontal region inside said container by analyzing reflected light from said third horizontal region through said open top, said third horizontal region comprising the upper portion (40b) of said sidewall, said necking area, and said flange,
means operative upon a determinination by said first, second, or third determining means that a defect is present for rejecting said container from said conveyor line.

7. A system for inspecting the inside surfaces of a container for defects, said container moving on a conveyor line and said container having an open top, a flange (20), a neck (30), a sidewall (40), a moat (50), a chime (70) and a dome bottom (60), said system comprising:
first means (Unit1, C1) located at a first position on said conveyor line for determining through said open top whether said defects are present in a first horizontal region inside said container by analyzing reflected light from said first horizontal region through said open top, said first horizontal region comprising said moat and said chime,
second means (Unit 2, C2) located at a second position on said conveyor line for determining through said open top whether said defects are present in a second horizontal region inside said container by analyzing reflected light from said second horizontal region through said open top, said second horizontal region comprising the lower portion (40a) of said sidewall and said dome,
third means (Unit 3, C3) located at a third position on said conveyor line for determining through said open top whether said defects are present in a third horizontal region inside said container by analyzing reflected light from said third horizontal region through said open top, said third horizontal region comprising the upper portion (40b) of said sidewall, said neck, and said flange,
means operative upon a determination by said first, second, or third determining means that a defect is present for rejecting said container from said conveyor line.

8. A system for inspecting the inside surfaces of a container for defects, said container having an open top, a flange (20), a necking area (30), a sidewall (40), a moat (50), a chime (70) and a dome bottom (60), said system comprising:

first means (Unit1, C1) for determining through said open top whether said defects are present in a first horizontal region inside said container, said first horizontal region comprising said moat and said chime, second means (Unit 2, C2) for determining through said open top whether said defects are present in a second horizontal region inside said container, said second horizontal region comprising the lower portion (40a) of said sidewall and said dome, third means (Unit 3, C3) for determining through said open top whether said defects are present in a third horizontal region inside said container, said third horizontal region comprising the upper portion (40b) of said sidewall, said neck, and said flange, each of said first, second, and third means comprising:

a. a camera for capturing an image of a region in said container, b. a lens on said camera for focussing said camera in the aforesaid region, c. means for illuminating the inside of said container, d. means for sensing the presence of said container, e. means connected to said sensing means, said illuminating means, and said camera for activating both said illuminating means and said camera in order to capture said image from the aforesaid region when said sensing means senses said presence of said container, said activating means analyzing said captured image for the presence of said defects in preselected windows in said image, means operative upon a determination by said first, second, or third determining means that a defect is present for rejecting said container.

9. The system of claim 8 wherein said second determining means comprises a circular polarizer for reducing the amount of reflected light from said dome.

10. A method for inspecting the inside surface of the moat (50) of a can (10) through the open top of the can, said can having a dome bottom (60), said method comprising the steps of:

illuminating the inside of said can through the open top with light, locating the open top of the can under a camera, the camera having a lens focussed in the field of view for the moat, placing a mask in the field of view of the focussed camera to mask out light reflected from the dome, capturing an image of the illuminated moat with the camera, and analyzing the captured image for defects in the moat of the can.

11. A method for inspecting a selected area on the inside surface of an object through an opening in the object, the object having a reflective surface that interferes with the inspection of the selected area, said method comprising the steps of:

illuminating the inside of the object through the opening with light, locating the opening of the object under a camera, the camera having a lens focussed in the field of view for the selected area, placing a mask in the field of view of the focussed camera to mask out light reflected from the interfering reflective surface, capturing an image of the illuminated selected area with the camera, and analyzing the captured image of the selected area for defects.

12. A method for inspecting the inside surface of the flange (20) and necking area (30) of a can (10) through the open top of the can, said can having a dome bottom (60), said method comprising the steps of:

illuminating the inside of said can through the open top with light, locating the open top of the can under a camera, the camera having a lens focussed in the field of view for the flange and the necking area, placing an occluding dot in the field of view of the focussed camera to mask out light reflected from the dome, capturing an image of the illuminated flange and neck with the cameras, and analyzing the captured image for defects in the flange and necking area of the can.

13. A method for inspecting the inside surfaces of a container for defects, the container having an open top, a flange (20), a necking area (30), a sidewall (40), a moat (50), a chime (70) and a dome bottom (60), said method comprising the steps of:

detecting through the open top whether any defects are present in an image of a first horizontal region inside the container, the first horizontal region comprising the moat and the chime, detecting through the open top whether any defects are present in an image of a second horizontal region inside the container, the second horizontal region comprising the lower portion (40a) of the sidewall and the dome, detecting through the open top whether any defects are present in an image of a third horizontal region inside the container, the third horizontal region comprising the upper portion (40b) of the sidewall, the necking area, and the flange, rejecting the container in response to the detection of any defects in the first, second, or third horizontal regions.

14. A method for inspecting the inside surfaces of an object for defects, said method comprising the steps of:

detecting through the open top whether any defects are present in images of a plurality of horizontal regions inside the object, and rejecting the container in response to the detection of any defects in any one of the plurality of horizontal regions.

15. A system for inspecting a selected area on the inside surface of an object through an opening in the object, said system comprising:

means for illuminating the inside of the object through said opening with light, a camera centrally located to said illuminating means, said camera having a lens, means for locating the opening of said object under the lens of said camera, said lens being focussed in the field of view for the selected area, said camera capturing an image of the illuminated selected area, and means for analyzing said captured image of said selected area for defects.

16. The system of claim 15 wherein said object is a metal can.

17. The system of claim 15 further comprising means in said field of view of said focussed camera for masking out interfering reflected light.

18. The system of claim 15 further comprising a circular polarizer is placed after said illuminating means in said field of view.

19. The system of claim 15 wherein said object is a metal can and further comprising:
- means in said field of view of said focussed camera for masking out interfering reflected light, and
- a circular polarizer placed after said illuminating means in said field of view.

* * * * *